US00PP22554P2

(12) United States Plant Patent
Zerr

(10) Patent No.: US PP22,554 P2
(45) Date of Patent: Mar. 6, 2012

(54) *POINSETTIA* PLANT NAMED 'SYEP22866'

(50) Latin Name: *Euphorbia pulcherrima*
Varietal Denomination: SYEP22866

(75) Inventor: Katharina Zerr, Hillscheid (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/932,382

(22) Filed: Feb. 23, 2011

(51) Int. Cl.
*A01H 5/00* (2006.01)

(52) U.S. Cl. ..... Plt./307

(58) Field of Classification Search ..... Plt./307
See application file for complete search history.

*Primary Examiner* — Kent L Bell

(74) *Attorney, Agent, or Firm* — S. Matthew Edwards

(57) ABSTRACT

A new *Poinsettia* plant named 'SYEP22866' particularly distinguished by its intense red bract color, medium sized inflorescences with relatively many bracts and cyathia, dark-green foliage, leaves with only weak lobes, small to medium-sized, v-shaped and tight habit with relatively upright directed stems.

1 Drawing Sheet

Latin name of the genus and species of the plant claimed: *Euphorbia pulcherrima.*

Varietal denomination: 'SYEP22866'.

BACKGROUND OF THE NEW PLANT

The present invention comprises a new *Poinsettia* plant, botanically known as *Euphorbia pulcherrima*, and hereinafter referred to by the variety name 'SYEP22866'.

'SYEP22866' is a product of a planned breeding program. The new cultivar 'SYEP22866' has intense red bracts, medium sized inflorescences with relatively many bracts and many cyathia, dark green foliage, and compact, v-shaped habit with relatively strong, upright directed stems.

'SYEP22866' originated from a hybridization made in the summer of 2003 in a controlled breeding program in Hillscheid, Germany. The female parent was the proprietary plant '10049', not patented, having deep red flower color, dark green foliage, about medium sized habit, and early flowering.

The male parent of 'SYEP22866' was the proprietary plant designated No. '298', not patented, with bright red bracts, dark green foliage, leaves with strong lobes, and upright plant habit with strong branches.

The resulting seeds were sown in February through March 2004 and 'SYEP22866' was selected as one flowering plant within the progeny of the stated cross in November/December 2004 in a greenhouse in Hillscheid, Germany.

The first act of asexual reproduction of 'SYEP22866' had been accomplished when shoot tip cuttings were used from the initial selection in late July 2004, rooted and cultivated for the above mentioned small trial.

More cuttings were used from the selected plant from April through May 2005 and grafted onto rootstocks of the variety 'Maren', in order to improve the branching ability. Shoot tip cuttings from successfully grafted stems were used in the summer of summer of 2007. They were rooted and cultivated as branched plants for a small trial in the fall and winter of 2007.

Horticultural examination of plants grown from cuttings of the plant initiated in the summer of 2007 in Hillscheid, Germany, and continuing thereafter on a larger scale, has demonstrated that the combination of characteristics as herein disclosed for 'SYEP22866' are firmly fixed and are retained through successive generations of asexual reproduction.

A Plant Breeder's Right for this cultivar has been applied for in Switzerland. A Plant Breeder's Right has also been applied for in Canada on Mar. 8, 2010 (No. 10-6883). 'SYEP22866' has not been made publicly available more than one year prior to the filing of this application.

'SYEP22866' has not been observed under all possible environmental conditions. The phenotype may vary significantly with variations in environment such as temperature, light intensity and day length.

DESCRIPTION OF DRAWING

The accompanying photographic drawings show typical flower and foliage characteristics of 'SYEP22866' with colors being as true as possible with an illustration of this type.

DETAILED BOTANICAL DESCRIPTION

Figure 1:
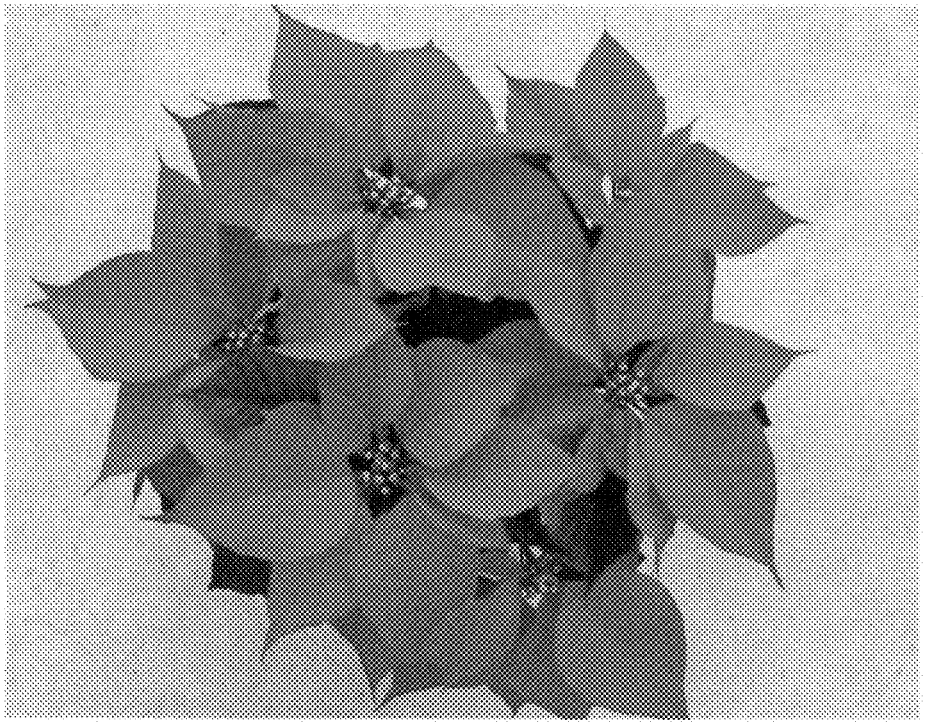
FIG. 1 shows a top view of the flower bracts of an about 17 week old plant taken on Nov. 19, 2010 at Lucas Greenhouses, Monroeville, N.J.
Figure 2:
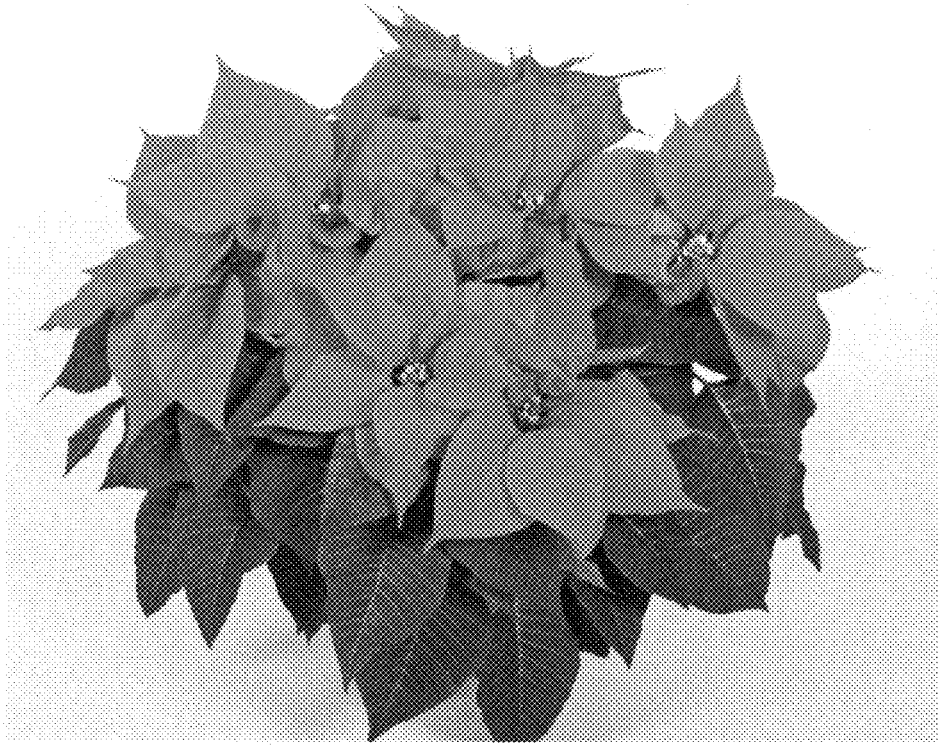
FIG. 2 shows a whole flowering plant. The picture had been taken in Hillscheid, Germany, on Nov. 12, 2008. It shows a 15 week old plant in a 14 cm pot.

The measurements were taken in Enkhuizen, Netherlands, on Dec. 16, 2010 on about 18 week old plants growing in a greenhouse. Culture of these plants had started on August 10 by planting rooted cuttings into 12 cm pots and pinching them about 2 weeks later. The plants were grown under natural day light in the fall (no black cloth was applied to initiate earlier flowering) and at the moderately warm temperature of 18°-20° C. for the bench heating.

Color Chart used: Royal Horticultural Society Colour Chart (R.H.S.) 2001

BRIEF SUMMARY OF INVENTION

The following observations, measurements, and comparisons describe plants grown on benches in a greenhouse in Hillscheid, Germany. The following traits have been repeatedly observed and are determined to be basic characteristics of the new variety. The combination of these characteristics distinguishes this *Poinsettia* plant as a new and distinct variety.

1. Intense red flower bract color
2. Medium sized inflorescences with relatively many bracts and many cyathia
3. Dark green foliage, weakly lobed leaves
4. Small to medium sized, well-branched and tight, mounding plant habit
5. V-shaped habit with relatively upright directed stems
6. Early to medium flowering response
7. Well suited for production of smaller plants without 'rings' (generally used for stabilisation and to avoid breaking off of branches) and good transportation ability

DIFFERENCES BETWEEN THE NEW VARIETY 'SYEP22866' AND SIMILAR VARIETIES

'SYEP22866' has roughly similar inflorescences and similar bract color as 'Fisolymp', U.S. Plant Pat. No. 14,662, but differs in plant habit. 'SYEP22866' is distinctly more compact with better transportation ability, while 'Fisolymp' tends to develop a wider plant habit.

In comparison to 'Fiscor Dark Red', U.S. Plant Pat. No. 12,723, 'SYEP22866' has bracts and leaves with no or less distinct lobes, and with narrower, more upright plant habit.

Compared with the commercial variety 'Christmas Feelings', U.S. Plant Pat. No. 14,618 under the designation 'NPCW02044', 'SYEP22866' develops a more compact plant habit, has a somewhat deeper red bract color, and inflorescences with longer bracts and more cyathia.

Plant:

*Form, growth and habit.*—Shrub, relatively compact and mounding plant habit, well-branched with upright directed stems.

*Plant height* (*without pot*).—24.5 cm.

*Plant width.*—33 cm.

*Number of branches.*—7.8.

*Number of inflorescences.*—7.5.

Root:

*Number of days to produce a rooted cutting/liner/young plant.*—24-25 days at a temperature of 22-24 degrees centigrade.

*Form.*—Self-branching, somewhat fleshy.

*Color.*—Near RHS N155B.

Stem:

*Color of stem* (*middle/main part*).—RHS 146A, with relatively strong infusion of anthocyanin: RHS 181A; shoot tips and young stems are light green RHS 143B to 143C, without anthocyanin.

*Length of stem.*—Approximately 17-22 cm.

*Diameter.*—0.5-0.6 cm.

*Length of internodes.*—From 2.0-2.5 cm.

*Texture.*—Smooth, glabrous.

Foliage:

*Arrangement.*—Alternate.

*Quantity.*—6-7 leaves per branch.

*Aspect.*—Most petioles are horizontally directed, while the leaf blades show downwards.

*Growing leaves, color upper surface.*—RHS 137D, or near RHS 143A tones.

*Growing leaves, color lower surface.*—RHS 137D.

*Mature leaves, color upper surface.*—Dark green, near RHS 139A.

*Mature leaves, color lower surface.*—RHS 137B.

*Leaf length.*—9.8 cm.

*Leaf width.*—7.2 cm.

*Shape.*—Ovate, with only weak expression of lobes.

*Base shape.*—Rounded to obtuse.

*Apex shape.*—Acuminate.

*Margin.*—Entire, apart from the lobes, that usually have rounded tips.

*Texture* (*both surfaces*).—Flat, smooth, apart from the protruding veins on the under-side, upper surface appears glabrous, lower side is covered with very short, fine hair.

*Venation pattern.*—Pinnate.

*Color of veins, upper surface.*—Approximately RHS 181B at base, else indistinct.

*Color of veins, lower surface.*—From RHS 181B near base fading to RHS 181D near leaf tip.

*Petiole color, upper surface.*—RHS 59A.

*Petiole color, lower surface.*—RHS 59B.

*Petiole length.*—5.0-7.5 cm.

*Diameter of petiole.*—2.5-3 mm.

*Texture upper and lower surfaces.*—Smooth, glabrous.

Inflorescence:

*Type.*—Terminal cyme with surrounding whorl of colored bracts.

*Flowering, botanically* (*opening of the stamina, shedding of pollen*).—From late November.

*Flowering period, commercially* (*sufficiently colored bracts*).—From mid to late November.

*Flowering response time.*—8-9 weeks from equinox.

*Duration of flowering.*—Depends from light and environment, at least 4-8 weeks of 'shelf' life.

*Fragrance.*—None/absent.

*Shape of inflorescence.*—Star-shaped arrangement, with the bracts well overlapping and slanting a little upwards.

*Diameter of inflorescence.*—21.1 cm.

*Inflorescence, vertical diameter.*—Approximately 4-5 cm.

*Number of completely colored bracts per inflorescence* (*sized over 2 cm*).—12-15.

*Single bract, shape.*—Ovate, with very weak distinctness of lobes.

*Bract, apex.*—Acuminate.

*Bract, base.*—Obtuse to rounded.

*Margin.*—Entire.

*Single bract, length of blade.*—11.0 cm, younger bracts diminishing in size.

*Single bract, width of blade.*—7.3 cm.

*Bract color, upper side.*—RHS 46B.

*Bract color, lower side.*—RHS 46C.

*Venation pattern.*—Pinnate.

*Vein color, upper surface.*—RHS 46A at the base, else indistinct.

*Vein color, lower surface.*—From RHS 51B to 51C, or near RHS 145B.

*Bract petiole length.*—About 1.5-2.3 cm, shorter for the younger bracts.

*Bract petiole diameter.*—2-3 mm.

*Petiole color, upper surface.*—Near RHS 53A.

*Petiole color, lower surface.*—Near RHS 144B, partly with tones of RHS 174B.

*Texture of bract*.—Both surfaces smooth, apart from the protruding veins on the underside, glabrous.

Cyme (true inflorescence):

*Cyme, diameter*.—About 1.5 cm in this trial, 1.5-2.5 cm elsewhere.

*Number of cyathia*.—5-10 in this trial, 10-15 have elsewhere been observed, borne in a tight cluster.

*Cyathium, shape*.—Ovate.

*Cyathium, diameter*.—5-6 mm.

*Cyathium, length*.—6-7 mm.

*Color*.—Mainly RHS 143A, top is red, RHS 46B.

*Peduncle length*.—2-4 mm.

*Peduncle color*.—RHS 143B.

*Nectar cups*.—Usually one per cyathium.

*Nectur cup, width*.—Mostly 6-7 mm.

*Nectar cup, color*.—Golden yellow, RHS 15A.

Reproductive organs:

*Stamen* (*actually reduced male florets*).—Usually in a small bunch of 10-20 at the top of the cyathium.

*Shape*.—Strap-like.

*Filament length*.—2-3 mm.

*Filament color*.—RHS 46A.

*Anther color*.—Yellow, RHS 11A.

*Anther diameter*.—1 mm.

*Pollen quantity*.—Moderate (normal quantity).

*Pollen color*.—RHS 12A.

*Pistils* (*actually female flowers*).—One per cyathium, occurrence depends much on light intensity, appears (if at all) about 4 weeks later than the stamen.

*Stigma shape*.—Trifurcate, 6-lobed.

*Style and stigma color*.—Dark red, RHS 46A.

*Ovary shape*.—Initially nearly round, later distinctly 3-cornered, 3 ovules.

*Ovary size*.—6-8 mm in diameter.

*Ovary color*.—RHS 143B.

*Fertility/seed set*.—No seed set observed.

Disease/pest resistance:

Disease resistance or susceptibility has not been observed on this hybrid.

What is claimed is:

1. A new and distinct variety of *Poinsettia* plant named 'SYEP22866', substantially as illustrated and described herein.

* * * * *